US011260156B2

(12) United States Patent
Weaver et al.

(10) Patent No.: US 11,260,156 B2
(45) Date of Patent: Mar. 1, 2022

(54) PRESSURE RELIEF MECHANISM FOR SORBENT CANISTERS

(71) Applicant: Fresenius Medical Care Holdings, Inc., Waltham, MA (US)

(72) Inventors: Colin Weaver, Pleasanton, CA (US); Daniel Schmidt, Petaluma, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 139 days.

(21) Appl. No.: 16/697,634

(22) Filed: Nov. 27, 2019

(65) Prior Publication Data

US 2021/0154387 A1  May 27, 2021

(51) Int. Cl.
*A61M 1/16* (2006.01)
*A61M 1/36* (2006.01)

(52) U.S. Cl.
CPC ........ *A61M 1/1696* (2013.01); *A61M 1/1603* (2014.02); *A61M 1/3639* (2013.01); *A61M 2205/3334* (2013.01)

(58) Field of Classification Search
CPC .............. A61M 1/1658; A61M 1/1603; A61M 1/1696; A61M 1/3639; A61M 2205/3334; B01D 36/001
See application file for complete search history.

(56) References Cited

U.S. PATENT DOCUMENTS

| 5,178,179 A | 1/1993 | Polaschegg et al. |
| 5,762,782 A | 6/1998 | Kenley et al. |
| 8,137,553 B2 * | 3/2012 | Fulkerson ........... A61M 1/3643 210/321.71 |
| 8,597,505 B2 * | 12/2013 | Fulkerson ............. A61M 1/166 210/86 |
| 8,960,010 B1 | 2/2015 | Crnkovich et al. |
| 9,354,640 B2 | 5/2016 | Byler |
| 9,757,505 B2 | 9/2017 | Lindley et al. |

(Continued)

FOREIGN PATENT DOCUMENTS

EP     2 444 365 A1     4/2012

OTHER PUBLICATIONS

International Patent Application No. PCT/US2020/062353, International Search Report (dated Mar. 25, 2021).

*Primary Examiner* — Terry K Cecil
(74) *Attorney, Agent, or Firm* — Leydig, Voit & Mayer, Ltd.

(57) ABSTRACT

A sorbent canister utilized when performing a dialysis treatment during hemodialysis (HD) or peritoneal dialysis (PD) is provided. The sorbent canister includes inlet and outlet ports that include a threaded interface for connection to inlet and outlet tubes for circulation of dialysate through the sorbent canister. Upon disconnection from a dialysis machine, a pressure relief cap can be threaded onto the threaded interface to seal the fluid in the sorbent canister while allowing for off-gases to be expelled when a pressure within the sorbent canister exceeds a threshold pressure, thereby preventing a rupture in the canister body. In one embodiment, the pressure relief cap includes a deformable insert with a hole formed therein that is closed in an uncompressed state and opened in a compressed state. In another embodiment, the pressure relief cap includes a diaphragm that mates with a feature of the inlet or outlet port.

9 Claims, 10 Drawing Sheets

(56) References Cited

U.S. PATENT DOCUMENTS

| | | |
|---|---|---|
| 9,833,554 B2 | 12/2017 | Crnkovich et al. |
| 9,867,918 B2 | 1/2018 | Merchant et al. |
| 9,962,477 B2 | 5/2018 | Slade |
| 10,019,020 B2 | 7/2018 | Byler |
| 10,398,826 B2 | 9/2019 | Lindley et al. |
| 10,441,704 B2 | 10/2019 | Crnkovich et al. |
| 10,603,421 B2 | 3/2020 | Merchant |
| 2009/0124963 A1 | 5/2009 | Hogard et al. |
| 2012/0018430 A1 | 1/2012 | Bork |
| 2018/0214627 A1 | 8/2018 | Kloeffel et al. |

\* cited by examiner

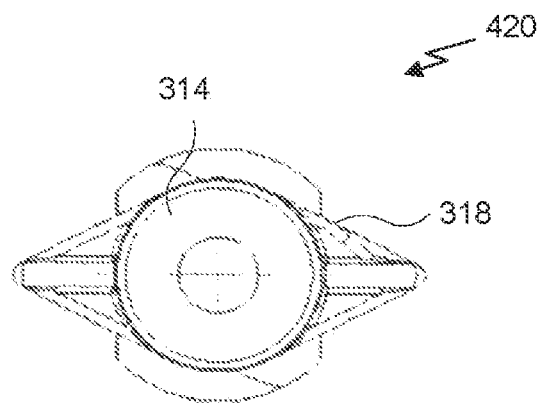
*Fig. 5A*
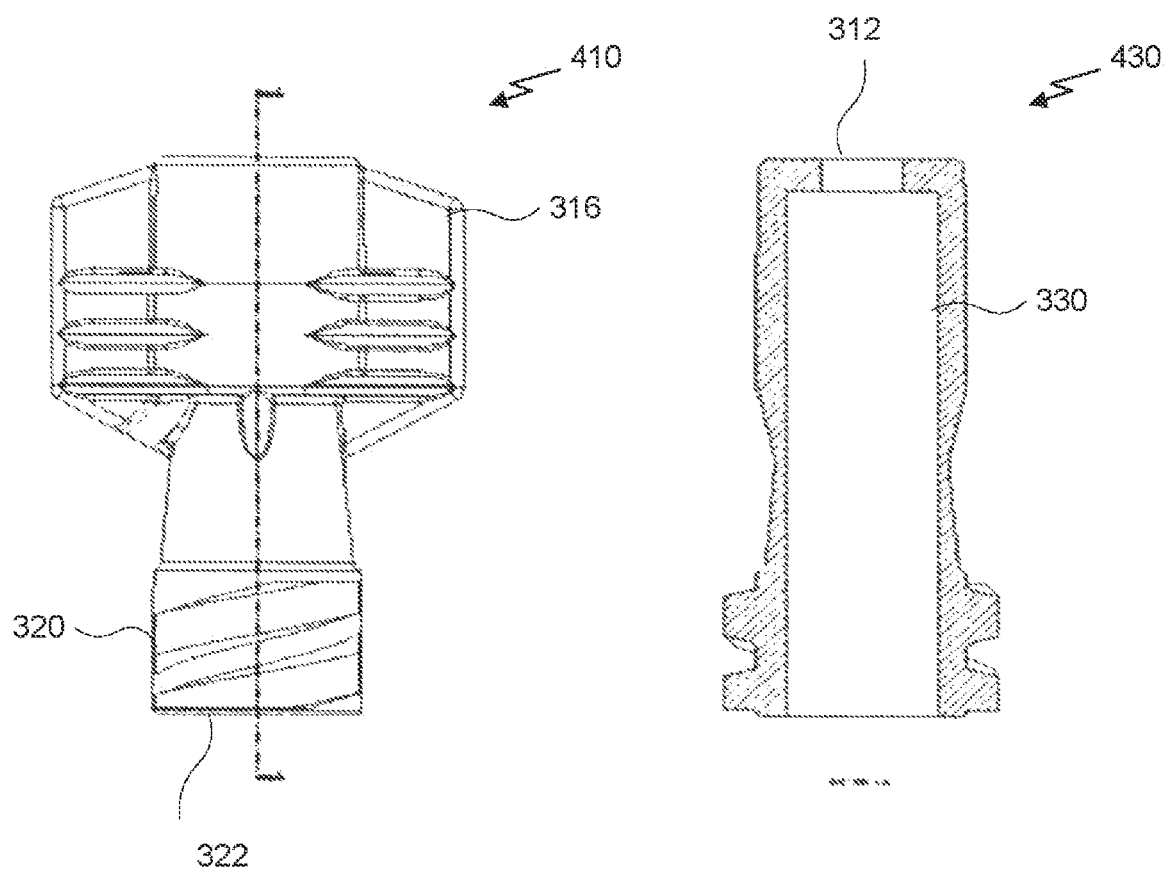
*Fig. 5B*
*Fig. 5C*

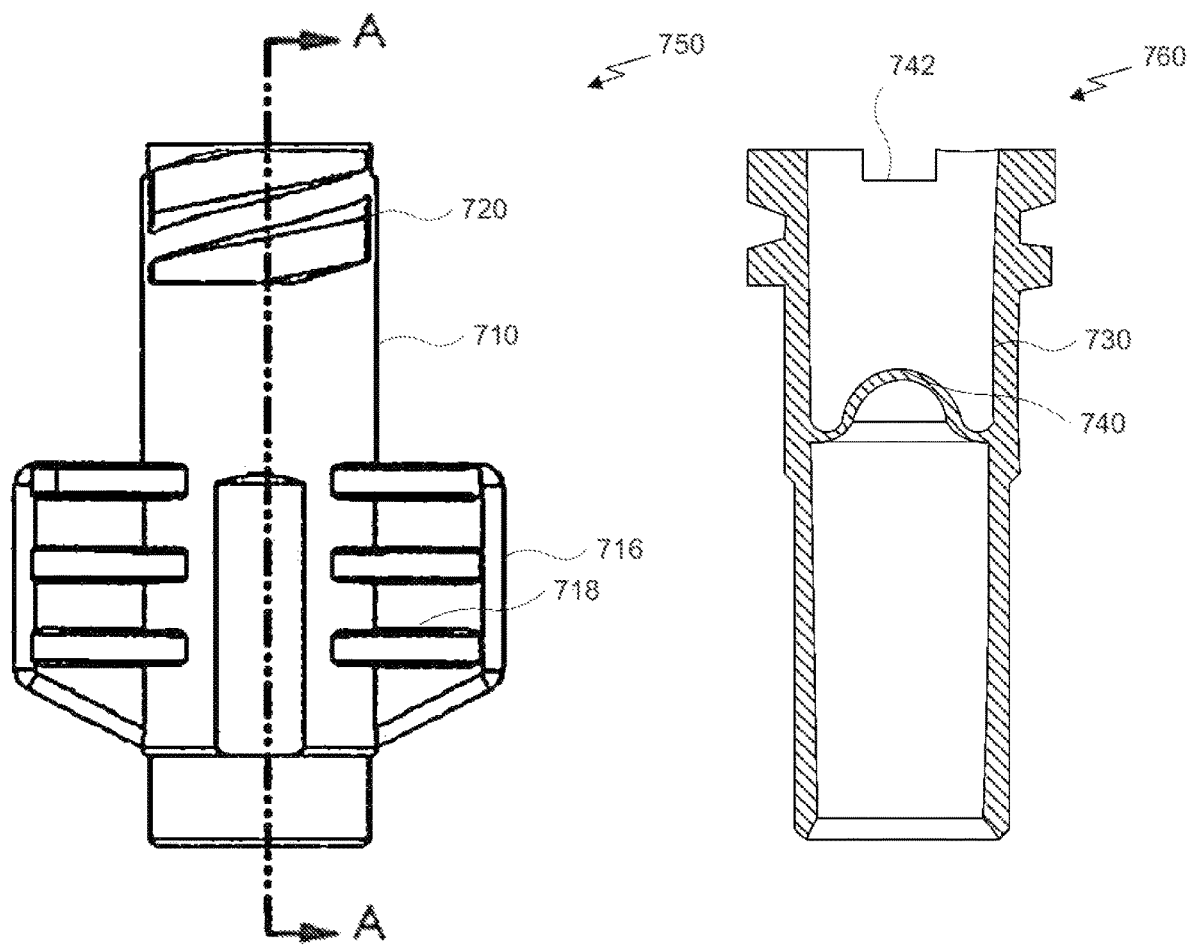
*Fig. 8A*  *Fig. 8B*

PRESSURE RELIEF MECHANISM FOR SORBENT CANISTERS

BACKGROUND

Patients with kidney failure or partial kidney failure typically undergo kidney dialysis, often at a hemodialysis (HD) treatment center. When healthy, kidneys maintain the body's internal equilibrium of water and minerals (e.g., sodium, potassium, chloride, calcium, phosphorous, magnesium, and sulfate). Patients with kidney failure tend to accumulate substantial excess water and toxins (e.g., urea, ammonia) in their blood and tissues and may experience serious mineral imbalances. The kidneys also function as part of the endocrine system to produce the hormone erythropoietin, as well as other hormones. Hemodialysis is an imperfect treatment to replace kidney function, in part, because it does not address the endocrine functions of the kidney.

In hemodialysis, blood is withdrawn from the patient through an intake needle (or catheter) which draws blood from an artery in a specific access site (e.g., arm, thigh, subclavian region, etc.). The arterial blood is then pumped through extracorporeal tubing typically via a peristaltic pump, and then through a special filter termed a "dialyzer." The dialyzer is designed to remove toxins such as urea, nitrogen, potassium, and excess water from the blood. As blood enters the dialyzer, it distributes into thousands of small-diameter, straw-like, generally-parallel fibers that run the length of the dialyzer. The walls of each fiber are formed from a semi-permeable membrane material with numerous small pores. Dialysate, a solution of chemicals and water, flows through the dialyzer in the spaces outside this network of fibers and generally in a direction opposite (i.e., counter-current with) the flow of the blood. As the dialysate flows through the dialyzer, it bathes and surrounds the fibers. These pores in fiber membranes are large enough to pass water and water-borne impurities—including minerals, urea and other small molecules—but are not large enough to pass red blood cells. Fresh dialysate thus accumulates excess impurities passing by diffusion across the membranes, and also collects excess water through an ultrafiltration (UF) process due to a hydrostatic pressure difference across the membrane (i.e., due to a higher hydrostatic pressure in the blood as compared to the dialysate).

During this process, the volume of the relatively-large cells and larger proteins in the blood remains within the fibers to be recirculated back to the body. Used dialysate exits the dialyzer with excess fluids and toxins via an output tube, thus cleansing the blood and red cell volume flowing through the dialyzer. The cleansed, dialyzed blood then flows out of the dialyzer via tubing and a needle (or catheter) back into the patient (e.g., into an adjacent vein at the same access site). Sometimes, a heparin drip or pump is provided along the extracorporeal blood flow loop to prevent red cell clotting during hemodialysis.

Conventional dialysis systems are provided with a volume of dialysate that is passed through the dialyzer and the used dialysate (e.g., effluent) is then directed to a drain bag, collection reservoir, or into a plumbing system (e.g., sink or toilet) of the treatment center. It will be appreciated that a large volume of dialysate (e.g., 400-600 L/treatment) can pass through the dialyzer during treatment. However, some dialysis systems can implement a dialysate regeneration system where the used dialysate is pumped through a canister filter, which can be referred to as a sorbent canister or a sorbent column, to cleanse the dialysate via adsorption of the toxins/waste, ion exchange, or catalytic conversion such that the filtered dialysate can be mixed with additional electrolytes and be re-circulated through the dialyzer. Such dialysate regeneration systems can significantly reduce the amount of dialysate that is required for treatment.

The sorbent canister is a replaceable component that must be changed periodically as waste or toxins build up in the filter media. The sorbent canisters typically have an inlet port and an outlet port that connect to tubes of the dialysis system. Fluid is likely to remain in the sorbent canister after it is disconnected from the dialysis system. Furthermore, the filter media and the fluid can continue to react and generate gases after being disconnected. If the inlet and outlet ports are left open so that such gases can escape the sorbent canister, then the fluid could also leak out of the sorbent canister causing issues with containment of the biohazard waste. Thus, the inlet and outlet ports are typically sealed when the tubes are disconnected from the canisters. However, the off-gases that continue to accumulate within the sorbent canister can build up pressure within the sorbent canister to the point that the sorbent canister can rupture.

SUMMARY

In an exemplary embodiment, the disclosure provides a sorbent canister for utilization in a dialysis system. The sorbent canister includes a canister body, including an inlet port and an outlet port, and at least one pressure relief cap coupled to one or more of the inlet port and the outlet port. The pressure relief cap is configured to open a fluid path from the inlet port or the outlet port to an external environment of the canister body when a pressure within the canister body exceeds a threshold pressure.

In an exemplary embodiment, the pressure relief cap includes a cap body with a recess formed therein that allows fluid to flow through a first end of the recess and a deformable insert that is inserted into the recess. The cap body includes a surface disposed at a second end of the recess, the surface including a hole formed therein, and the deformable insert is inserted adjacent to the surface to prevent fluid flow between the first end of the recess and the hole. In a compressed state, the deformable insert allows fluid flow between the first end of the recess and the hole. The deformable insert can be formed from a silicone material. In an embodiment, the recess is cylindrical and the deformable insert is a cylinder having a hole formed along an axial length of the cylinder. The hole is closed in the uncompressed state, and the hole is opened in the compressed state. The hole is configured to open when a fluid pressure in the first end of the recess exceeds the threshold pressure such that the fluid pressure compresses the deformable insert against the surface at the second end of the recess.

In another exemplary embodiment, at least one of the inlet port and the outlet port incorporates a male taper connection, and the pressure relief cap includes a cap body with a recess formed therein that allows fluid to flow through a first end of the recess. The cap body includes a convex surface disposed at a second end of the recess, and the convex surface contacts and forms a seal against a top surface of the male taper connection when the cap body is threaded into one of the inlet port or the outlet port. In an embodiment, the convex surface is characterized as separating from the top surface of the male taper when a fluid pressure within an interior fluid pathway connected to a hole formed in the top surface of the male taper exceeds the threshold pressure, the separation forming a fluid path from the interior fluid pathway, through a gap between an exterior surface of the male taper and an interior surface of the recess, to the external environment proximate a thread interface between the cap body and the inlet port or outlet port.

BRIEF DESCRIPTION OF THE DRAWINGS

FIGS. 5A-5C show front, top, and section views of the pressure relief cap, in accordance with an embodiment.

FIGS. 8A & 8B show front and section views of a pressure relief cap, respectively, in accordance with another embodiment.

DETAILED DESCRIPTION

A challenge in providing optimal dialysis treatment is the filtering or transport of sterile dialysate fluid needed for treatment. A dialysis treatment facility may need to install expensive reverse osmosis (RO) and deionization (DI) filtration systems in order to produce large amounts of RO/DI filtered water that are mixed with electrolytes or other chemicals to provide the clean dialysate solution that is pumped through the dialyzer to remove waste and toxins from the patient's blood. Even if the treatment facility does not produce the dialysate on-site, large amounts of fluid must be transported and stored at the treatment facility to accommodate multiple patients. Sorbent canisters can reduce the amount of required fluid for treatments significantly, which reduces the size of the filtration system or can reduce the amount of dialysate that needs to be stored on-site at the treatment facility. The sorbent canisters can also be utilized at a patient's home in peritoneal dialysis (PD) systems that reduce the number of bags of dialysate that must be delivered to the patient.

Exemplary embodiments of the present disclosure provide a sorbent canister which prevents the fluid from leaking while allowing for pressure within the canister to be relieved as needed.

In an embodiment, the disclosure provides a pressure relief cap for use with a sorbent canister included in a dialysis system. In some embodiments, the pressure relief cap can be removable. In other embodiments, the pressure relief cap can include an interface for connection to the dialysis system. In such embodiments, the pressure relief cap, once installed on the sorbent canister, remains attached to the inlet and/or outlet ports of the sorbent canister during dialysis treatment.

In an embodiment, the pressure relief cap includes a recess formed in a cap body. A deformable insert is pressed into the recess. The deformable insert includes a hole formed therein that is closed in an uncompressed state and opened in a compressed state. Consequently, when the pressure in the recess of the pressure relief cap exceeds a threshold pressure, the hole is opened and fluid or gas can escape the sorbent canister through the hole in the pressure relief cap.

In another embodiment, the pressure relief cap includes a diaphragm feature that forms a seal against a tapered feature included in the inlet port or outlet port of the canister body. When a pressure in the recess of the pressure relief cap exceeds a threshold pressure, the diaphragm feature deflects to release the seal, allowing fluid or gas to escape out a threaded interface of the pressure relief cap.

Figure 1:
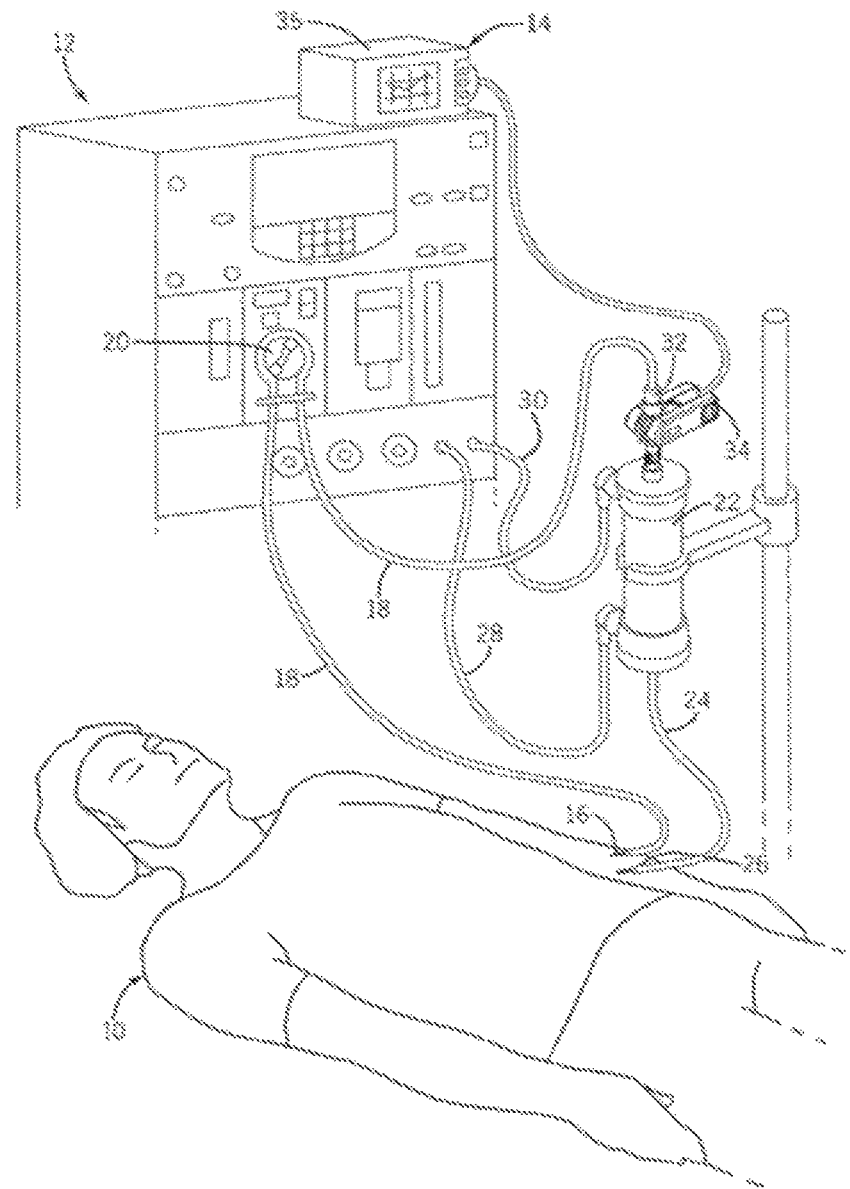
FIG. 1 illustrates a patient undergoing hemodialysis in a clinical setting, in accordance with the prior art.

FIG. 1 illustrates a patient 10 undergoing hemodialysis treatment using a conventional hemodialysis system 12, as well as a non-invasive, optical blood monitor 14. A typical hemodialysis clinic will have several hemodialysis systems 12 for treating patients, e.g., on a Monday-Wednesday-Friday schedule or a Tuesday-Thursday-Saturday schedule. While the scope of this disclosure is not limited to a particular number of hemodialysis systems located at a clinic, or a specific type of dialysis system, the general operation of the hemodialysis system 12 is helpful for understanding an exemplary environment in which embodiments may be utilized.

An input needle or catheter 16 is inserted into an access site of the patient 10, such as in the arm, and is connected to extracorporeal tubing 18 that leads to a peristaltic pump 20 and then to a dialyzer or blood filter 22. The dialyzer 22 removes toxins and excess fluid from the patient's blood. The dialyzed blood is returned from the dialyzer through extracorporeal tubing 24 and return needle or catheter 26. In some parts of the world, the extracorporeal blood flow may receive a heparin drip to prevent clotting although that is not shown in FIG. 1. The excess fluids and toxins are removed by clean dialysate liquid which is supplied to the dialyzer 22 via tube 28 and removed for disposal via tube 30. A typical hemodialysis treatment session takes about 3 to 5 hours in the United States.

In some embodiments, the optical blood monitor 14 includes a blood chamber 32, an optical blood sensor assembly 34, and a controller 35. The blood chamber 32 is preferably located in line with the extracorporeal tubing 18 upstream of the dialyzer 22. Blood from the peristaltic pump 20 flows through the tubing 18 into the blood chamber 32. The preferred sensor assembly 34 includes light-emitting diode (LED) photo emitters that emit light at substantially 810 nm, which is isobestic for red blood cell hemoglobin, at substantially 1300 nm, which is isobestic for water, and at substantially 660 nm, which is sensitive for oxygenated hemoglobin. The blood chamber 32 includes lenses so that the sensor emitters and detectors can view the blood flowing through the blood chamber 32, and determine the patient's real-time hematocrit value and oxygen saturation value using ratiometric techniques generally known in the prior art.

For purposes of background, when a typical patient 10 arrives at a hemodialysis clinic, the patient is first checked in and then weighed on a scale at the clinic. The patient then is seated in an assigned hemodialysis chair where a clinician inserts an arterial and venous needle into the patient's access. The access may be an artificial shunt or a natural fistula that has been surgically tied from an artery to a vein. Alternatively, as mentioned previously, the connection might be through a catheter. Next, the dialysis lines 18, 24 are prefilled with normal saline and connected to the patient. The peristaltic pump 20 is started slowly and the normal saline is flushed through the lines 18, 24 as well as the dialyzer 22 into the patient 10, as arterial blood is pulled into the dialysis circuit. The normal saline tends to lubricate or prime the system for blood passage. Also, since saline is less dense than blood, any leaks in the system will be immediately apparent before starting the hemodialysis process. In the exemplary environment of FIG. 1, the peristaltic pump 20 is shown as a blood pump, and a dialysate pump is not shown. A dialysate pump may be provided in hemodialysis system 12 in addition to the blood pump. Examples of systems with both a dialysate pump and a peristaltic pump are described, for example, in U.S. Pat. Nos. 8,597,505 and 8,137,553 which are both incorporated by reference in their entireties. In other implementations, a dialysate pump is not necessary and dialysate flows through tubing 30 using gravity.

Figure 2:
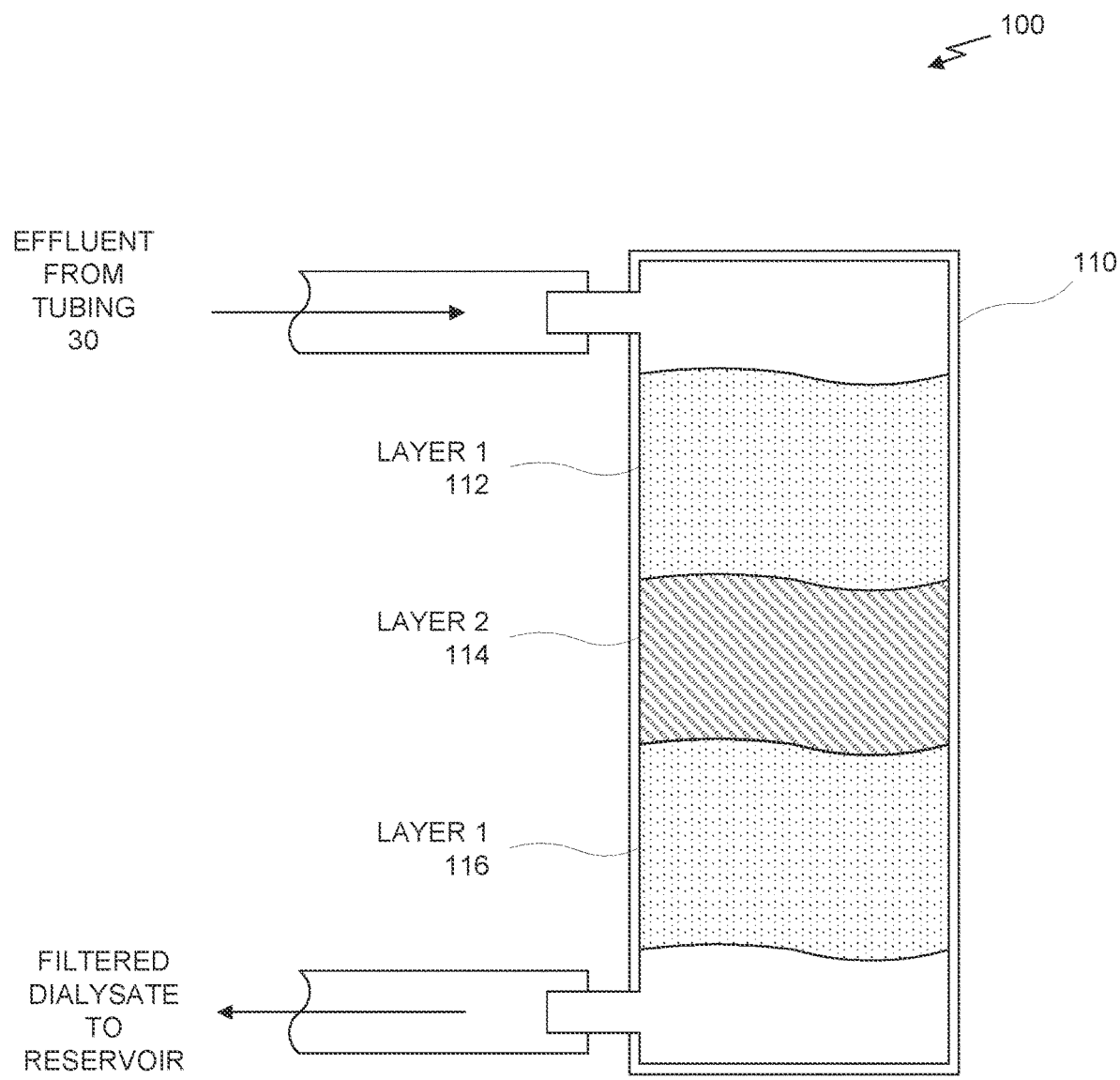
FIG. 2 illustrates a filtration system for a dialysis system, in accordance with the prior art.

FIG. 2 illustrates a filtration system 100 for a dialysis system, in accordance with the prior art. With conventional dialysis systems, as effluent (e.g., dialysate with additional waste and toxins) is removed from the dialyzer 22 through tube 30, the effluent is disposed in a collection vessel or into a drain. However, in a dialysate regeneration dialysis system, the effluent can be filtered through a sorbent canister 110 that contains a number of layers of filter media (e.g., 112, 114, 116, etc.). The filter media can include mechanical as well chemical or biological filtration media such as polysulfone, activated carbon, zeolite, ion-exchange resins, or the like. Although three layers of filter media are shown in FIG. 2, different embodiments of the sorbent canister 110 can include different numbers or arrangement of filter media.

In order to pass through the filter media, the effluent is pumped under pressure from a pump. In some embodiments, a peristaltic pump attached to tubing 28 supplies sufficient pressure to push the effluent through the filter media. In other embodiments, the effluent in tubing 30 is supplied to another pump, which increases the pressure of the effluent entering the sorbent canister 110. The additional pump may be required where the operating pressure through the dialyzer 22 is not sufficient for pushing the effluent through the filter media in the sorbent canister 110, but the operating pressure required of the sorbent canister 110 may be too high for the dialyzer 22.

In some embodiments, the filtered fluid exiting the sorbent canister 110 is not clean dialysate, but is merely a treated wastewater where most of the toxins, waste, or remaining electrolytes have been removed and/or neutralized by the filter media. This treated wastewater may be sufficient to be mixed with new electrolytes to generate new dialysate that can be pumped back to the dialyzer 22 through tubing 28. In some embodiments, the treated wastewater can be passed through additional filters such as an ultraviolet (UV) filter for sterilization. In some embodiments, the treated wastewater is pumped into a collection reservoir where peristaltic pumps are configured to draw treated water from the reservoir and mix the treated water with a concentrated electrolyte solution in order to produce new dialysate.

Figure 3:
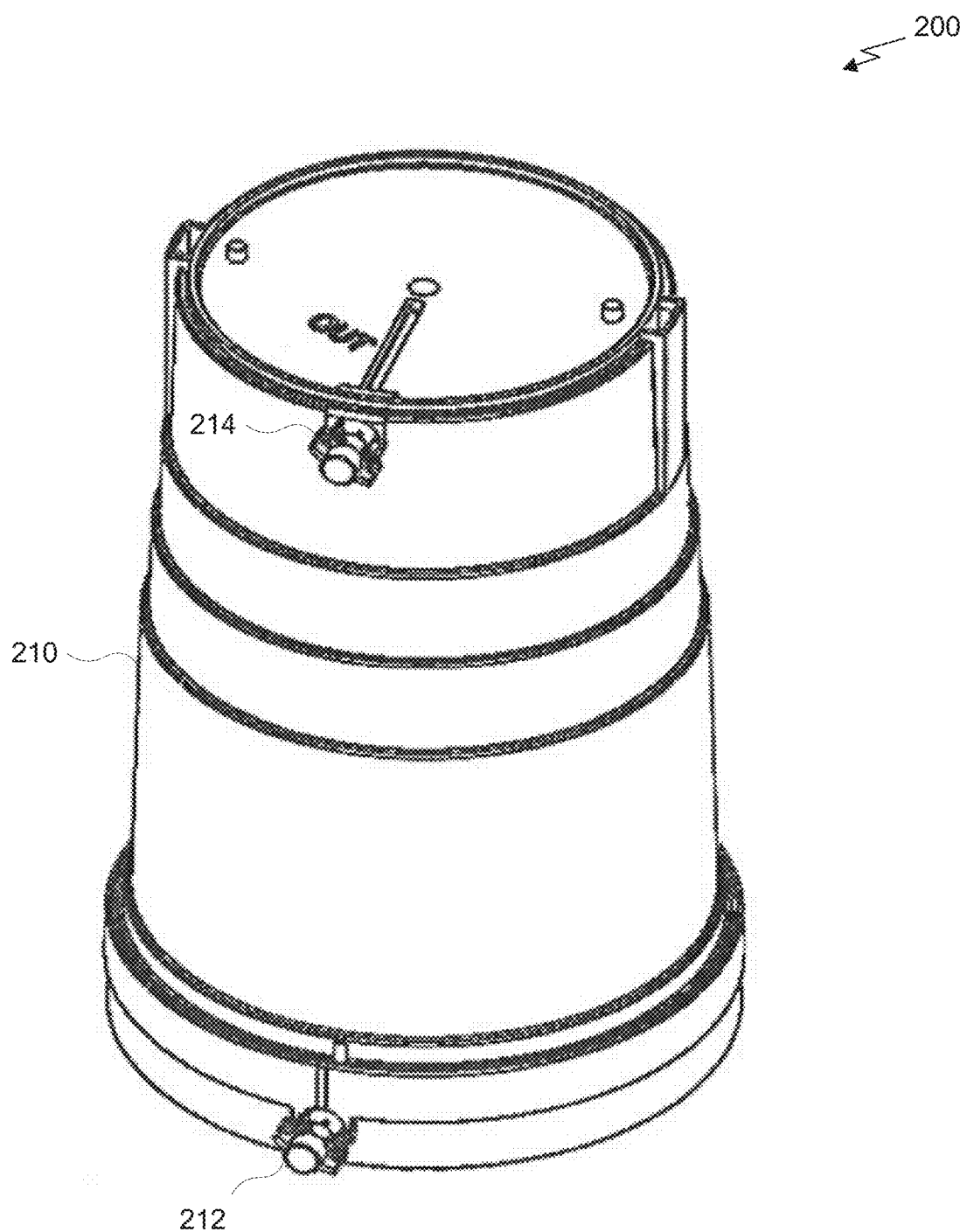
FIG. 3 illustrates a sorbent canister, in accordance with an embodiment.

FIG. 3 illustrates a sorbent canister 200, in accordance with an embodiment. The sorbent canister 200 includes a canister body 210 that can be formed from a thermoplastic material such as high density polyethylene (HDPE) using an injection molding technique. It will be appreciated that, in other embodiments, the canister body 210 can be formed from other materials, such as polyvinyl chloride (PVC), polyethylene (PE), polypropylene (PP), or the like. Although not typically made for disposable applications, the canister body 210 can also be formed from metals such as a 316 series stainless steel.

In an embodiment, the sorbent canister 200 includes an inlet port 212 and an outlet port 214. The inlet port 212 is formed in the side of the canister body 210. Although the inlet port 212 is shown proximate the bottom of the canister body 210 and the outlet port 214 is shown proximate the top of the canister body 210, in other embodiments, the arrangement of the inlet port 212 and the outlet port 214 may be switched, or both the inlet port 212 and the outlet port 214 can be formed in the top surface of the canister body 210. Any arrangement or number of inlet ports 212 or outlet ports 214 are contemplated as within the scope of the present disclosure.

It will be appreciated that, as depicted in FIG. 3, the inlet port 212 and the outlet port 214 are shown detached from any tubing, with caps attached to the port connectors. Such an arrangement is typical for storage or disposal of the sorbent canister 200. In some embodiments, the caps include a tapered interface such as a Luer connector as described by standard ISO 594. For example, a male Luer connector is formed at or otherwise attached to each of the inlet port 212 and/or the outlet port 214. Tubing can then be attached to the sorbent canister 200 by attaching a female Luer connector to the tubing such that the tubing can be easily connected or disconnected from the canister. The caps can then also comprise a female Luer connector that can easily be attached to the male Luer connector of the port when disconnected.

It will be appreciated that any interface can be implemented for connecting tubing to the sorbent canister 200, including threaded connectors and tapered, conical interfaces. Further, the caps provided can be sealed such that liquids or gases are sealed inside the sorbent canister 200 when the caps are in place. When sealing a container and trapping gas inside the container, care must be taken to ensure that the container is safe if the gas inside the container is allowed to expand. Gases can expand when heated or when chemical reactions between the dissolved components of the liquids in the sorbent canister 200 continue to react with the filter media. One solution to this issue is to build a pressure relief mechanism into the caps utilized with the sorbent canister 200.

Figure 4:
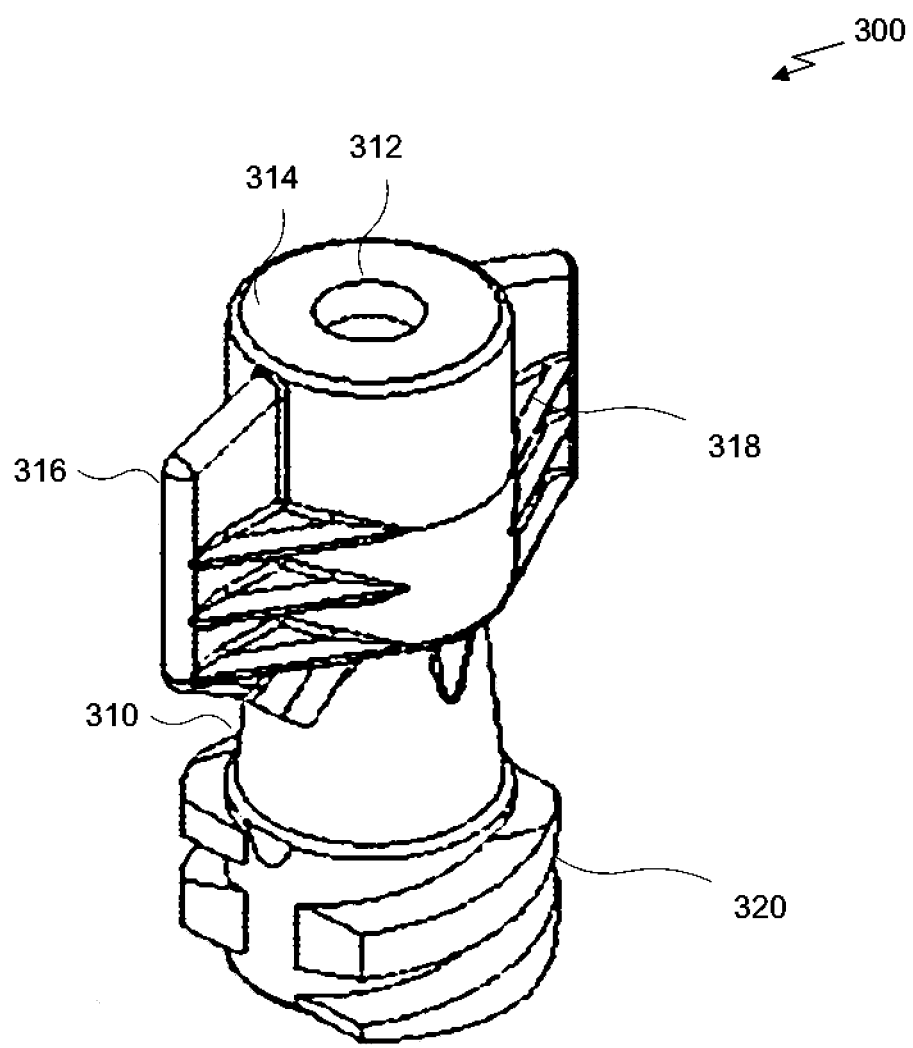
FIG. 4 is an isometric view of a pressure relief cap for a sorbent canister, in accordance with an embodiment.

FIG. 4 is an isometric view of a pressure relief cap 300 for a sorbent canister, in accordance with an embodiment. As depicted in FIG. 4, the pressure relief cap includes a cap body 310 with a number of features formed thereon. The cap body 310 is substantially cylindrical with a major axis that is substantially axial with a fluid flow through the cap body 310. A hole 312 is formed in a top surface 314 of the cap body 310. Furthermore, a pair of bosses 316 are attached to an exterior surface of the cap body 310 proximate the top surface 314. Each boss 316 is structurally reinforced by a number of ribs 318.

A threaded interface 320 is formed on the exterior surface of the cap body 310 proximate a bottom surface 322 (not visible in FIG. 4) of the cap body 310. The threaded interface includes threads that are discontinuous around the circumference of the cap body 310. In some embodiments, the threads are slotted or a portion of the threads are missing in one or more locations around the circumference of the cap body 310. In other embodiments, the threads do not include the slot or are continuous around the entire circumference of the cap body 310. The threaded interface 320 is designed to mate with a corresponding threaded interface formed in the inlet port 212 or outlet port 214 of the sorbent canister 200.

FIGS. 5A-5C show front 410, top 420, and section 430 views of the pressure relief cap 300, in accordance with an embodiment. The section view 430 shows a recess 330 formed in an interior of the cap body 310. A first end of the recess 330 is proximate a bottom surface 322 of the cap body 310 and a second end of the recess 330 is proximate a top surface 314 of the cap body 310. Fluid can pass through the recess from the first end to the second end and exit the cap body 310 through the hole 312. In an embodiment, the recess 330 has a tapered or conical shape that is designed to form a seal with a corresponding tapered feature in the inlet port 212 or outlet port 214 of the sorbent canister 200. In another embodiment, the recess 330 is cylindrical.

Figure 6B:
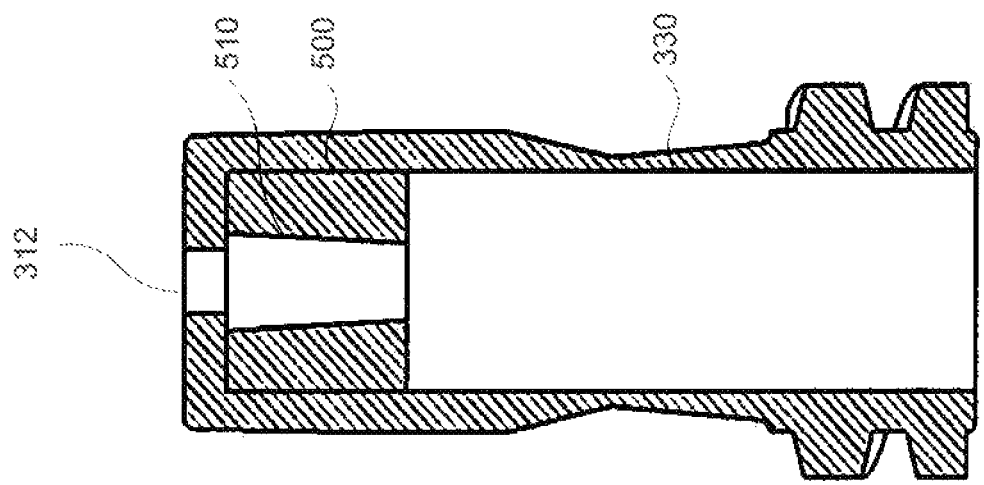
FIGS. 6A & 6B illustrate a deformable insert pressed into the recess of the cap body 310, in accordance with an embodiment.
Figure 6A:
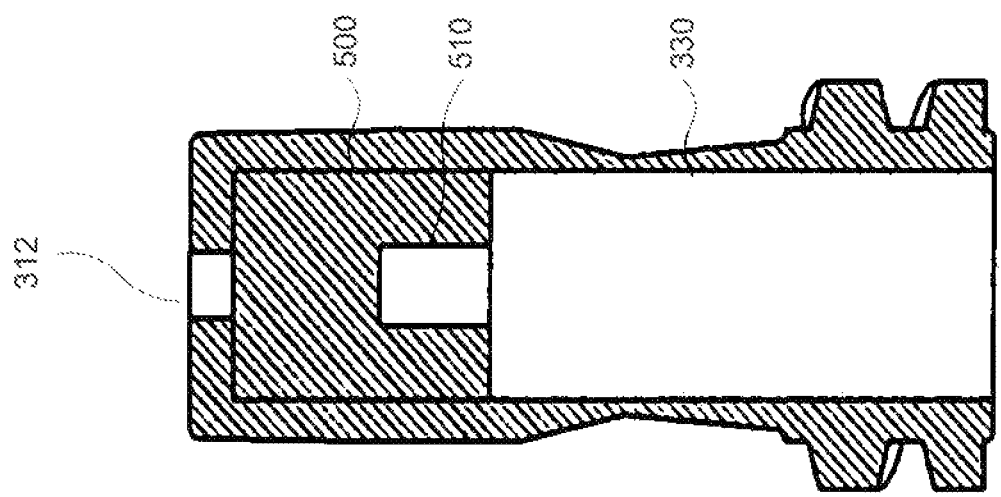

FIGS. 6A & 6B illustrate a deformable insert 500 pressed into the recess 330 of the cap body 310, in accordance with an embodiment. The deformable insert 500 can be formed from an elastomeric material such as silicone or high density foams. The deformable insert 500 can have a hole 510 formed therein that is coaxial with a substantially cylindrical shape of the deformable insert 500. As depicted in FIG. 6A, when the deformable insert 500 is in an uncompressed state, the hole 510 is closed, thereby preventing fluid from flowing from the first side of the recess 330 to the hole 312. In contrast, as depicted in FIG. 6B, when the deformable insert 500 is in a compressed state, the hole 510 is open, thereby allowing fluid to flow from the first side of the recess 330 to the hole 312.

The deformable insert 500 can be compressed by a fluid pressure inside the recess 330 against an interior surface of the cap body at the second end of the recess 330 opposite the top surface 314. A threshold pressure that causes the hole 510 to open can be tuned by controlling selection of the base resin material, adjusting the processing parameters of the manufacturing process (e.g., curing time, temperature, pressure, etc.), and adjusting the feature geometry of either the insert 500, the recess 330, or both the insert 500 and the recess 330. By controlling the characteristics of the deformable insert 500 during manufacture, the pressure relief cap 300 operates as a pressure relief valve that allows fluid or gas to escape from the sorbent canister 200 when a fluid pressure inside the sorbent canister 200 exceeds the threshold pressure. It will also be appreciated that different deformable inserts can be manufactured corresponding to different threshold pressures and, by installing a particular deformable insert in the cap body 310, a particular threshold pressure can be selected for a particular application.

Figure 7:
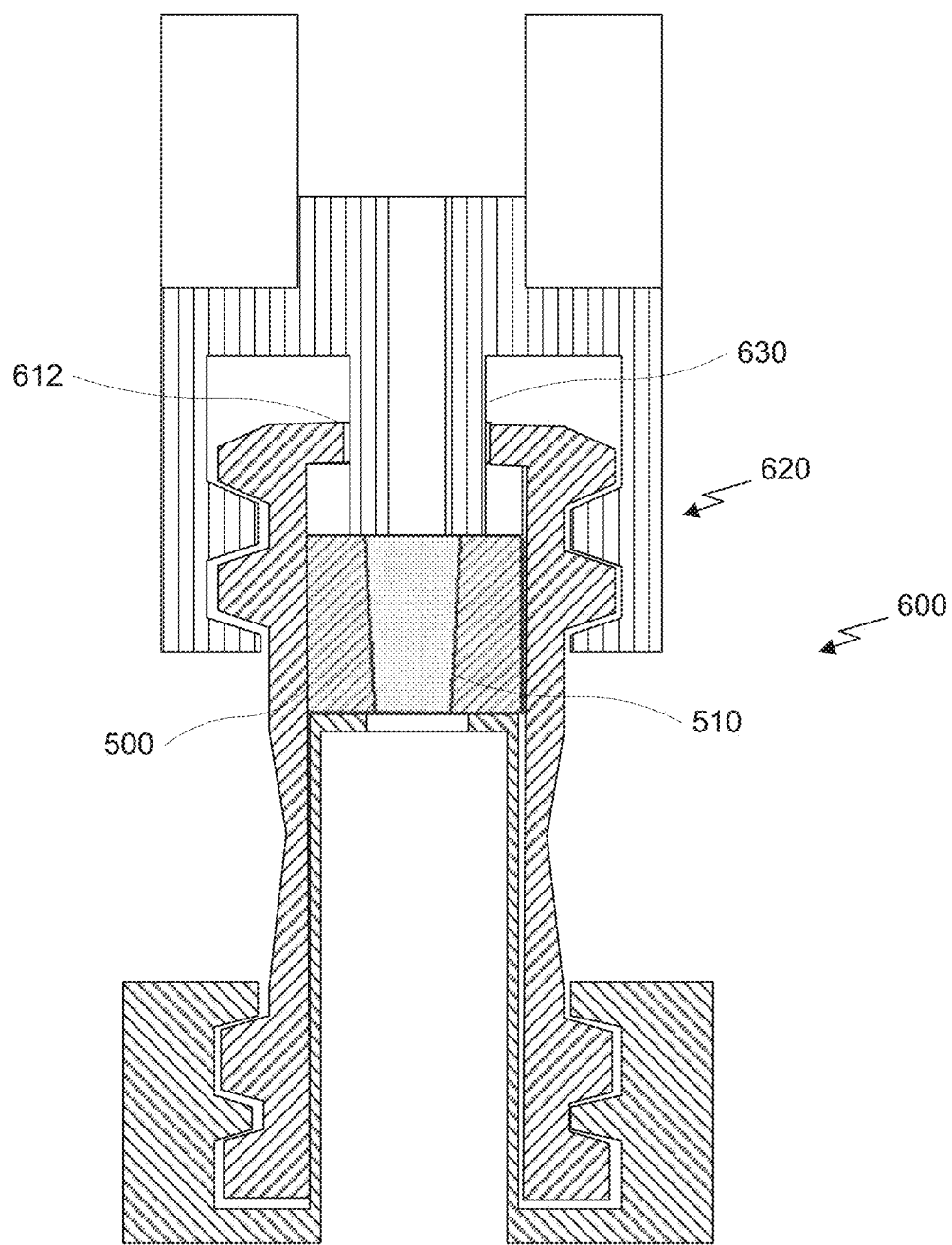
FIG. 7 shows a pressure relief cap configured to operate as a bi-directional valve, in accordance with an embodiment.

Although the pressure relief cap 300 is designed as a one-way valve for releasing pressure from an interior volume of the sorbent canister 200 to an external environment outside of the sorbent canister 200, the mechanism of the deformable insert 500 can function as a bi-directional valve. FIG. 7 shows a pressure relief cap 600 configured to operate as a bi-directional valve, in accordance with an embodiment. The pressure relief cap 600 can be designed to be attached to the inlet port 212 or outlet port 214 of the sorbent canister 200 semi-permanently. An interface 620 can be formed proximate the hole 612 in the cap body 610 that allows the tubing to be connected to the top of the pressure relief cap 600. As shown in FIG. 7, the interface 620 can be a threaded interface. In some embodiments, the interface 620 comprises a male or female Luer connector, and tubing can be attached to a corresponding female or male Luer connector, respectively.

As shown in FIG. 7, the connector that attaches to the interface includes a boss 630 that is inserted into the hole 612 such that the boss 630 compresses the deformable insert 500 against a surface of a feature of the inlet port 212 or outlet port 214 that is inserted into the recess 630 in the cap body 610. By mechanically compressing the deformable insert 500, the hole 510 is opened and allows for bi-directional flow of fluid into or out of the sorbent canister 200. When the tubing is disconnected from the interface, the deformable insert relaxes to fill the space in the recess and returns to the uncompressed state, once again acting as a pressure relief valve to release fluid pressure from the interior of the sorbent canister 200 into the external environment when the fluid pressure exceeds the threshold pressure.

It will be appreciated that such configurations essentially build the pressure relief function into the inlet port or outlet port of the sorbent canister 200 and do not require a technician or nurse to seal the port by attaching the pressure relief cap 300 after disconnecting the tubing from the port. Although the pressure relief cap 600 is shown as being threaded into the port, a more permanent type of connection such as using an adhesive, plastic weld, or press fit can also be used to secure the pressure relief cap 600 to the port.

FIGS. 8A & 8B shows front 750 and section 760 views of a pressure relief cap 700, respectively, in accordance with another embodiment. The pressure relief cap 700 is not designed to include the deformable insert 500 in order to provide a pressure relief mechanism. Instead, the pressure relief cap 700 includes a diaphragm feature 740 that interfaces with a top surface of a tapered boss implemented in the inlet port 212 or outlet port 214 of the sorbent canister 210.

As depicted in FIG. 8A, the pressure relief cap 700 includes a cap body 710, a threaded interface 720, and a pair of bosses 716 supported by ribs 718. A recess 730 is formed in a top surface of the cap body. The diaphragm feature 740 is formed at a bottom surface of the recess 730. It will be appreciated that the terms "top" and "bottom" as used herein can be flipped depending on the orientation of the pressure relief cap 700 and only represent relative directions as shown in the Figures. In an embodiment, the diaphragm feature 740 can be formed as a convex surface that protrudes into the recess 730. The diaphragm feature 740 can be made from the same material as the cap body 710 and integrated therein by forming the feature during an injection molding process. In another embodiment, the diaphragm feature 740 can be a separate component that can be pressed into the recess 730. For example, the diaphragm feature 740 can be, essentially, a Belleville washer with no center hole pressed into the recess 730 and formed from a thin metal material.

Figure 9B:
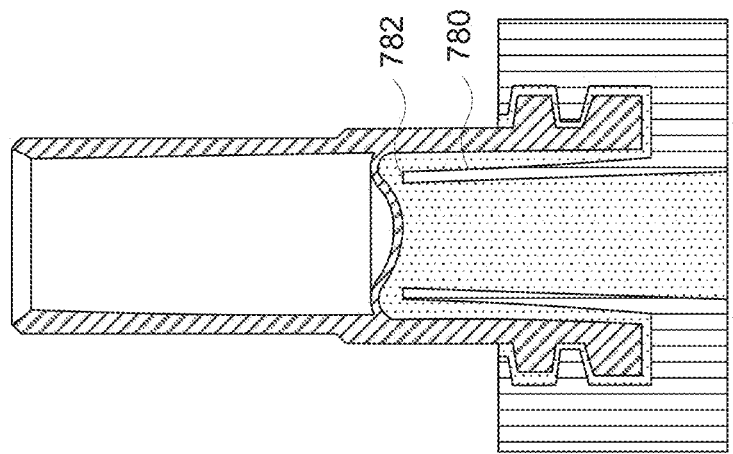
FIGS. 9A & 9B illustrate the pressure relief mechanism of the pressure relief cap 700, in accordance with some embodiments.
Figure 9A:
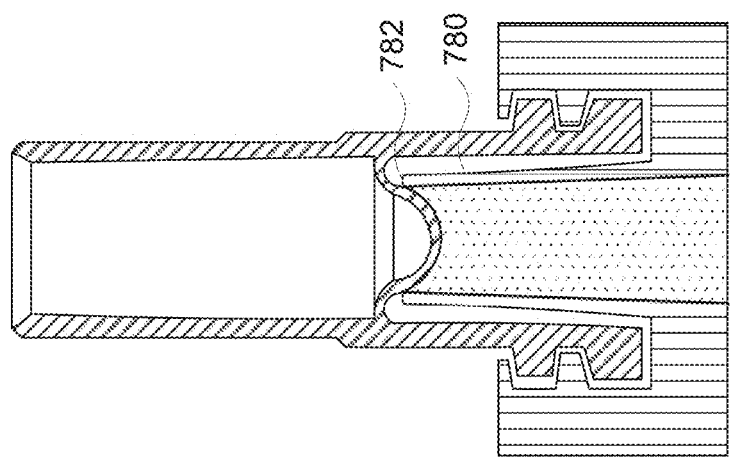

FIGS. 9A & 9B illustrate the pressure relief mechanism of the pressure relief cap 700, in accordance with some embodiments. As depicted in FIG. 9A, when the fluid pressure is below a threshold pressure, the diaphragm feature 730 creates a seal against a top surface 782 of a taper feature 780 in the inlet port or outlet port. As depicted in FIG. 9B, as the fluid pressure increases greater than the threshold pressure, the diaphragm feature 730 deflects away from the top surface 782 of the taper feature 780, releasing the seal. The fluid (or gas) can then flow between the taper feature and an inside surface of the recess 730. The fluid is able to flow around the threaded feature 720 and out into the external environment. In some cases, the threaded feature 720 is tight against a bottom surface of the corresponding mating threaded hole or the base of the taper feature in the port and, as a result, the fluid cannot flow out through the threads. In such cases, the notch 742 and/or slots formed in the threaded interface 720 can allow for a fluid flow pathway that bypasses the threads.

Figure 10:
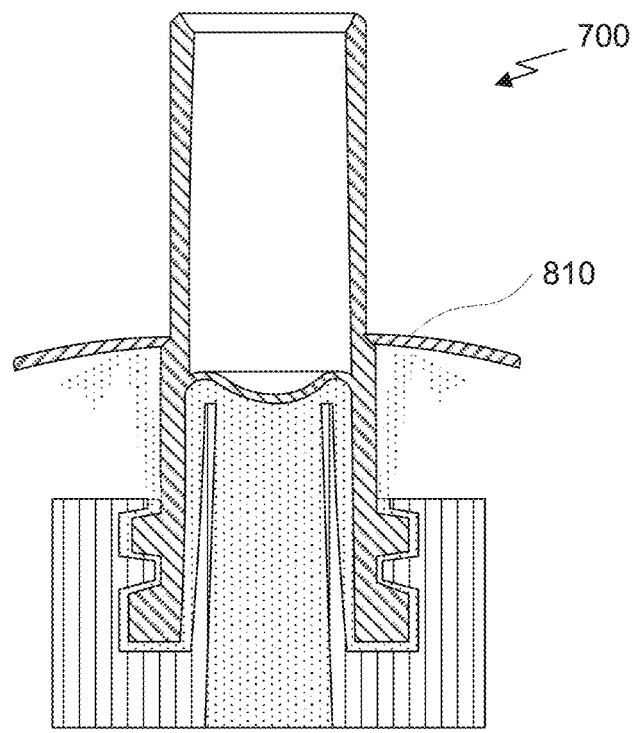
FIG. 10 illustrates a deflection feature integrated into the pressure relief cap, in accordance with some embodiments.

FIG. 10 illustrates a deflection feature 810 integrated into the pressure relief cap 700, in accordance with some embodiments. It will be appreciated that the high pressure and small orifice between the threads can act as a nozzle that lets fluid or gas exit the pressure relief cap 700 at high velocity. In order to avoid injury or significant dispersal of fluid containing bodily waste, a deflection feature 810 can be integrated into or otherwise attached to the pressure relief cap 700. In an embodiment, the deflection feature 810 can include a curved washer that is pressed onto the cap body 810. In other embodiments, the deflection feature 810 can be integrated into the cap body 810 as a feature of a mold during the injection molding process. In some embodiments, the deflection feature 810 can comprise any structural component that is placed in a fluid path that functions to re-direct the fluid path towards the canister body 210.

Although not shown in FIG. 10, a deflection feature can also be added to the pressure relief cap 300 or the pressure relief cap 600. The deflection feature can be permanently or semi-permanently attached to the pressure relief cap 300. However, in the case of the pressure relief cap 600, the deflection feature can comprise a removable component that can interface with the threaded interface 620 when the tubing is removed.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A sorbent canister for utilization in a dialysis system, the sorbent canister comprising:
   a canister body including an inlet port and an outlet port; and
   at least one pressure-relief cap coupled to one or more of the inlet port and the outlet port,
   wherein the pressure relief cap is configured to open a fluid path from the inlet port or the outlet port to an external environment of the canister body when a pressure within the canister body exceeds a threshold pressure, and
   wherein the pressure relief cap comprises:
      a cap body with a recess formed therein that allows fluid to flow through a first end of the recess, the cap body including a surface disposed at a second end of the recess, the surface including a hole formed therein; and
      a deformable insert that is inserted into the recess adjacent the surface, wherein, in an uncompressed state, the deformable insert prevents fluid flow between the first end of the recess and the hole, and wherein, in a compressed state, the deformable insert allows fluid flow between the first end of the recess and the hole.

2. The sorbent canister according to claim 1, wherein the deformable insert is formed from an elastomeric material.

3. The sorbent canister according to claim 1, wherein the deformable insert comprises a cylinder having a hole formed along an axial length of the cylinder, wherein the hole of the cylinder is closed in the uncompressed state and the hole of the cylinder is opened in the compressed state.

4. The sorbent canister according to claim 3, wherein the hole of the cylinder is configured to open when a fluid pressure in the first end of the recess exceeds the threshold pressure such that the fluid pressure compresses the deformable insert against the surface at the second end of the recess.

5. The sorbent canister according to claim 1, wherein the cap body includes threads formed on an external surface of the cap body proximate the first end of the recess, and wherein the threads are configured to be mated with corresponding threads formed in the inlet port or the outlet port of the canister body.

6. The sorbent canister according to claim 1, wherein the canister body is formed from a high density polyethylene (HDPE) material and the cap body is formed from a polyvinyl chloride (PVC) material.

7. A sorbent canister for utilization in a dialysis system, the sorbent canister comprising:
   a canister body including an inlet port and an outlet port; and
   at least one pressure-relief cap coupled to one or more of the inlet port and the outlet port,
   wherein the pressure relief cap is configured to open a fluid path from the inlet port or the outlet port to an external environment of the canister body when a pressure within the canister body exceeds a threshold pressure,
   wherein at least one of the inlet port and the outlet port incorporates a male connection, and
   wherein the pressure relief cap comprises:
      a cap body with a recess formed therein that allows fluid to flow through a first end of the recess, the cap body including a surface disposed at a second end of the recess, wherein the surface contacts and forms a seal against a top surface of the male connection when the cap body is threaded into one of the inlet port or the outlet port.

8. The sorbent canister according to claim 7, wherein the surface is characterized as separating from the top surface of the male connection when a fluid pressure within an interior fluid pathway connected to a hole formed in the top surface of the male connection exceeds the threshold pressure, the separation forming a fluid path from the interior fluid pathway, through a gap between an exterior surface of the male connection and an interior surface of the recess, to the external environment proximate a thread interface between the cap body and the inlet port or outlet port.

9. The sorbent canister according to claim 8, wherein the thread interface comprises threads formed on the exterior surface of the cap body proximate the first end of the recess, and wherein the threads are discontinuous such that a slot is formed along the length of the threads that allows fluid to move between the exterior surface of the cap body and a corresponding surface of the inlet port or outlet port.

* * * * *